United States Patent [19]

Gras et al.

[11] Patent Number: 5,550,206

[45] Date of Patent: Aug. 27, 1996

[54] POLYAMINES CONTAINING UREA GROUPS

[75] Inventors: Rainer Gras, Bochum; Elmar Wolf, Recklinghausen, both of Germany

[73] Assignee: Huels Aktiengesellschaft, Marl, Germany

[21] Appl. No.: 487,532

[22] Filed: Jun. 7, 1995

[30] Foreign Application Priority Data

Sep. 14, 1994 [DE] Germany .................. 44 32 637.8

[51] Int. Cl.$^6$ .................... C08G 12/06; C08G 14/08
[52] U.S. Cl. ................. 528/229; 528/59; 528/87; 528/93; 528/422
[58] Field of Search ................... 528/229, 422, 528/59, 87, 93

[56] References Cited

U.S. PATENT DOCUMENTS 4,916,201  4/1990  Harris et al. ..................... 528/60

Primary Examiner—Shelley A. Dodson
Attorney, Agent, or Firm—Oblon, Spivak, McClelland, Maier, & Neustadt, P.C.

[57] ABSTRACT

The present invention relates to novel polyamines containing urea groups and a process for the preparation of these polyamines, represented by the general formula:

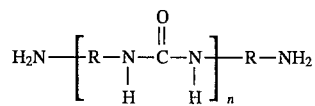

where n is: $2 \leq n \geq 1$; and R denotes an alkylene radical having 2–14 C atoms which may optionally be substituted by 1–3 $CH_3$ or $C_2H_5$ groups, or 1–3 $CH_2$ groups of the alkylene radical R may be substituted by —O—, —NH— or —$NCH_3$—.

3 Claims, No Drawings

POLYAMINES CONTAINING UREA GROUPS

BACKGROUND OF THE INVENTION

1. Field of the Invention

The present invention relates to novel polyamines containing urea groups and a process for the preparation of these polyamines.

2. Discussion of the Background

The epoxy resins based on bisphenol A and cured with polyamines are distinguished in practice by a number of desirable properties, such as, for example, good adhesion to all possible substrates, good solvent resistance and chemical resistance. These properties of the cured polyamine/epoxy mixtures could be further improved if the polyamines contained urea groups. The preparation of polyamines containing urea groups by condensation of 2 mol of polyamine and 1 mol of urea leads to solids or highly viscous products which cannot be processed without solvents.

SUMMARY OF THE INVENTION

It is thus the object of the present invention to provide a process which permits the preparation of polyamines which contain urea groups and are processable at room temperature with epoxy resins.

Surprisingly, this object could be achieved by condensing urea in the presence of a large excess of polyamine, of 1:(2–30), preferably 1:(5–20), and removing the unconverted polyamine from the reaction product comprising the polyamine containing urea groups, by evaporation in a thin-film evaporator.

The present invention thus relates to a polyamine containing a plurality of urea groups and having the following general formula:

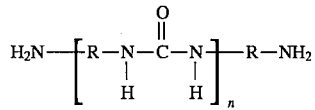

where n is: $2 \leq n \geq 1$; R represents an alkylene radical having 1–14 C atoms which may optionally be substituted by 1 to 3 $CH_3$ or $C_2H_5$ groups, or 1 to 3 $CH_2$ groups of the alkylene radical R may be substituted by —O—, —NH— or —$NCH_3$—.

The compounds according to the invention are characterized by a basic amine content of 4–14 mmol $NH_2$/g.

The concentration of urea groups in the polyamines according to the invention is 4–13 mmol/g. The viscosity of the compounds according to the invention at 25° C. varies from 5,000 to 100,000 mPas.

The present invention furthermore relates to a process for the preparation of polyamines which contain urea groups and are processable at room temperature, characterized in that urea is reacted with polyamines having the following composition:

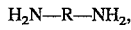

at a molar ratio of urea to polyamine of 1:(2–30), preferably 1:(5–20),in such a way that the mixture is first heated to 130°–150° C. until about 80% of the calculated amount of $NH_3$ has been liberated and is further heated slowly to 180°–220° C., preferably to 200° C. until $NH_3$ has been substantially quantitatively eliminated, and, after the reaction is complete, the unconverted polyamine is separated from the reaction product by evaporation in a thin-film evaporator at a temperature of 100°–180° C. and under a reduced pressure of between 0.05 to 0.2 mmHg, preferably of 0.1 mmHg; where R denotes an alkylene radical having 2–14 C atoms, which may optionally be substituted by 1–3 $CH_3$ or $C_2H_5$ groups, or 1–3 $CH_2$ groups of the alkylene radical R may be substituted by —O—, —NH— or —$NCH_3$ groups, The polyamines to be used for the purposes of the present invention are open-chain amines, such as, for example, ethylenediamine, 1,2-propanediamine, 1,3-diaminopropane, 1,4-diaminobutane, neopentanediamine, 2-methylpentamethylenediamine, 5-methylnonamethylenediamine, 4,7-dioxadecane-1,10-diamine, 4,9-dioxadodecane-1,12-diamine, 4,7,10-trioxatridecane-1,13-diamine, 2,2,4(2,4,4)-trimethylhexamethylenediamine, diethylenetriamine, dipropylenetriamine or N,N'-bis-(3-aminopropyl)-ethylenediamine.

In the process according to the invention, urea and the stated polyamines are reacted with one another in a molar ratio of 1:(5–20) and, after the reaction is complete, i.e. after elimination of $NH_3$, the unconverted polyamine is separated off in a second stage by evaporation in a thin-film evaporator.

In the condensation of the urea with the polyamine, the components are heated in the stated molar ratio at a temperature of 130°–150° C. until about 80% of the expected amount of $NH_3$ has been liberated. Thereafter, in order to complete the reaction, the mixture is heated slowly to 180°–220° C., preferably to 200° C. and is heated further until the elimination of $NH_3$ is quantitative. The reaction mixture is then cooled and, after intermediate storage at room temperature, the unconverted polyamine is removed at a temperature of 100°–180° C. and a reduced pressure of 0.05 to 0.2 mmHg, preferably of 0.1 mmHg by means of evaporation in a thin-film evaporator. The temperature at which the polyamine is separated off by evaporation in a thin-film evaporator depends on the boiling point of the polyamine to be separated off. The higher its boiling point, the higher is the temperature at which the polyamine is separated off in the thin-film evaporator (under a reduced pressure of about 0.05 to 0.2 mmHg).

The compounds according to the invention are exceptionally suitable for curing epoxy resins at room temperature.

DESCRIPTION OF THE PREFERRED EMBODIMENTS

For the purpose of illustration only, the invention will be described in connection with certain preferred embodiments. However, it is recognized that various modifications, changes, additions and improvements may be made in the preferred embodiments without departing from the spirit and scope of the invention.

GENERAL PREPARATION METHOD FOR THE CONDENSATION OF POLYAMINES WITH UREA

Area and a polyamine present in a molar ratio of 1:(5–20) are heated at about 150° C. with thorough stirring for about 5 hours until about 80% of the amount of $NH_3$ has been liberated. Thereafter, in order to complete the reaction, the temperature of the mixture is raised to 200° C. and kept at that temperature for about 1 hour. Most often, the reaction is completed under these conditions.

The ammonia liberated in the reaction is collected in a 2N $H_2SO_4$ solution, the content of which is tested at regular intervals. The reaction can be readily monitored in this way.

EXAMPLE 1 a) Urea was reacted with 2-methylpentamethylenediamine in a molar ratio of 1:8 under the conditions described in the general preparation method for the condensation of polyamines with urea. The reaction mixture had a basic amine content of 14.3 mmol $NH_2$/g.

b) The reaction mixture 1a was evaporated in a thin-film evaporator at 100° C. under vacuum of 0.1 mbar in order to separate off the unconverted 2-methylpentamethylenediamine. The reaction product, which remains as the residue after the evaporation in the thin-film evaporator, had a viscosity of 12,500 mPas at 25° C.; the basic amine content was 6.8 mmol $NH_2$/g; the 2-methylpentamethylenediamine content was 0.7%.

EXAMPLE 2 a) Urea was reacted with 2,2,4(2,4,4)-trimethylhexamethylenediamine (TMD) in a molar ratio of 1:10, as described in Example 1a. The reaction mixture had a basic amine content of 10.8 mmol $NH_2$/g.

b) The reaction mixture from 2a was evaporated in a thin-film evaporator at 110° C. and 0.1 mbar in order to separate off the unconverted TMD. The reaction product, the residue from the evaporation in the thin-film evaporator, had a viscosity of 70,000 mPas at 25° C.; the basic amine content was 5.1 mmol $NH_2$/g; the TMD content was 0.6%.

EXAMPLE 3 a) Urea was reacted with diethylenetriamine in a molar ratio of 1:10, as described in Example 1a. The reaction mixture had a basic amine content of 16.8 mmol $NH_2$/g.

b) The reaction mixture from 3a was evaporated in a thin-film evaporator at 100° C. and 0.1 mbar in order to separate off the unconverted diethylenetriamine. The reaction product had a viscosity of 15,200 mPas at 25° C.; the basic amine content was 11.5 mmol $NH_2$/g; the diethylenetriamine content was 0.6%.

EXAMPLE 4 a) Urea was reacted with 5-methylnonamethylenediamine in a molar ratio of 1:15, as described in Example 1a. The reaction mixture had a basic amine content of 10.5 mmol $NH_2$/g.

b) The reaction mixture from 4a was evaporated in a thin-film evaporator at 110° C. and under vacuum of 0.1 mbar in order to separate off the unconverted 5-methylnonamethylenediamine. The reaction product had a viscosity of 51,000 mPas at 25° C.; the basic amine content was 5.1 mmol $NH_2$/g; the 5-methylnonamethylenediamine content was less than 0.7%.

What is claimed as new and desired to be secured by Letters Patent of the United States is:

1. A polyamine containing urea groups represented by the formula:

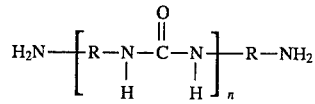

wherein n is: $2 \leq n \geq 1$; and R is a $C_{2-14}$ alkylene radical or a substituted $C_{2-14}$ alkylene radical with 1–3 $CH_3$ or $C_2H_5$ groups, or a $C_{2-14}$ alkylene radical where 1–3 —$CH_2$— groups are substituted by —NH— or —$NCH_3$— groups.

2. Process for preparing a polyamine containing urea groups and being processable at room temperature, comprising the steps of:

admixing a urea with a polyamine to form a mixture, heating said mixture at 130°–150° C. until about 80% of the calculated amount of $NH_3$ has been liberated;

further heating said mixture to 180°–220° C. until said $NH_3$ has been substantially removed thus forming a reaction product; and separating unconverted polyamine from said reaction product by evaporating said reaction product in a thin-film evaporator while maintaining an elevated temperature of 100°–180° C., under a reduced pressure;

wherein said polyamine is represented by the following formula:

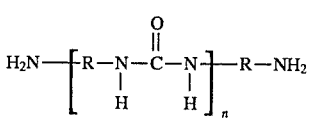

wherein n is: $2 \leq n \geq 1$; and

R is a $C_{2-14}$ alkylene radical or a substituted $C_{2-14}$ alkylene radical with 1–3 $CH_3$ or $C_2H_5$ groups, or a $C_{2-14}$ alkylene radical where 1–3 —$CH_2$— groups are substituted by —NH— or —$NCH_3$— groups, and wherein the molar ratio of said urea to said polyamine is 1:(2–30).

3. The polyamines containing urea groups of claim 1, wherein said polyamines are reacted with epoxy resins at room temperature to form cured epoxy resins.

* * * * *